US010555789B2

(12) United States Patent
Powell

(10) Patent No.: US 10,555,789 B2
(45) Date of Patent: Feb. 11, 2020

(54) PADDED MEDICAL PROCEDURE GLOVE

(71) Applicant: Latesha Simone Powell, Lawnside, NJ (US)

(72) Inventor: Latesha Simone Powell, Lawnside, NJ (US)

(*) Notice: Subject to any disclaimer, the term of this patent is extended or adjusted under 35 U.S.C. 154(b) by 120 days.

(21) Appl. No.: 15/493,763

(22) Filed: Apr. 21, 2017

(65) Prior Publication Data

US 2017/0304016 A1 Oct. 26, 2017

Related U.S. Application Data

(60) Provisional application No. 62/391,298, filed on Apr. 25, 2016.

(51) Int. Cl.
*A61B 42/10* (2016.01)
*A61B 42/20* (2016.01)

(52) U.S. Cl.
CPC .............. *A61B 42/10* (2016.02); *A61B 42/20* (2016.02)

(58) Field of Classification Search
CPC ......... A61B 42/10; A61B 42/20; A61B 42/00; A41D 19/0096; A41D 19/0055; A41D 19/015; A41D 19/01505; A41D 19/01547; A41D 19/0006; A41D 19/0058; A41D 19/0086; A41D 19/01517; B29D 99/0067
USPC .................. 2/20, 21, 163, 161.7, 161.8, 168
See application file for complete search history.

(56) References Cited

U.S. PATENT DOCUMENTS

| 4,845,780 | A  | * | 7/1989 | Reimers ............. A41D 19/0062 2/160 |
| 6,175,962 | B1 | * | 1/2001 | Michelson ......... A41D 19/0058 128/918 |
| 2012/0042429 | A1 | * | 2/2012 | Zare ....................... A61B 42/10 2/20 |
| 2014/0208481 | A1 | * | 7/2014 | Champagne ........... A61B 42/10 2/161.7 |
| 2014/0259283 | A1 | * | 9/2014 | Govindasamy ........ A61B 42/10 2/161.7 |
| 2015/0189932 | A1 | * | 7/2015 | Champagne ........... A41D 13/08 2/161.6 |

FOREIGN PATENT DOCUMENTS

| WO | WO-2013016785 A1 * | 2/2013 | ............. A61B 42/10 |
| WO | WO-2014120972 A1 * | 8/2014 | ............. A61B 42/10 |

* cited by examiner

*Primary Examiner* — Alissa L Hoey
*Assistant Examiner* — Patrick J. Lynch

(57) ABSTRACT

A glove may be formed of a polymer and include one or more pads over the back side of one or more distal finger joints. The glove may optionally be lubricated, sterile, reversible and/or disposable, and may incorporate indicia indicating the location of the pads. The pads may provide protection from, e.g., repetitive stresses in tapping vials or syringes in medical examination, surgery, laboratory procedures, or other clinical contexts.

5 Claims, 1 Drawing Sheet

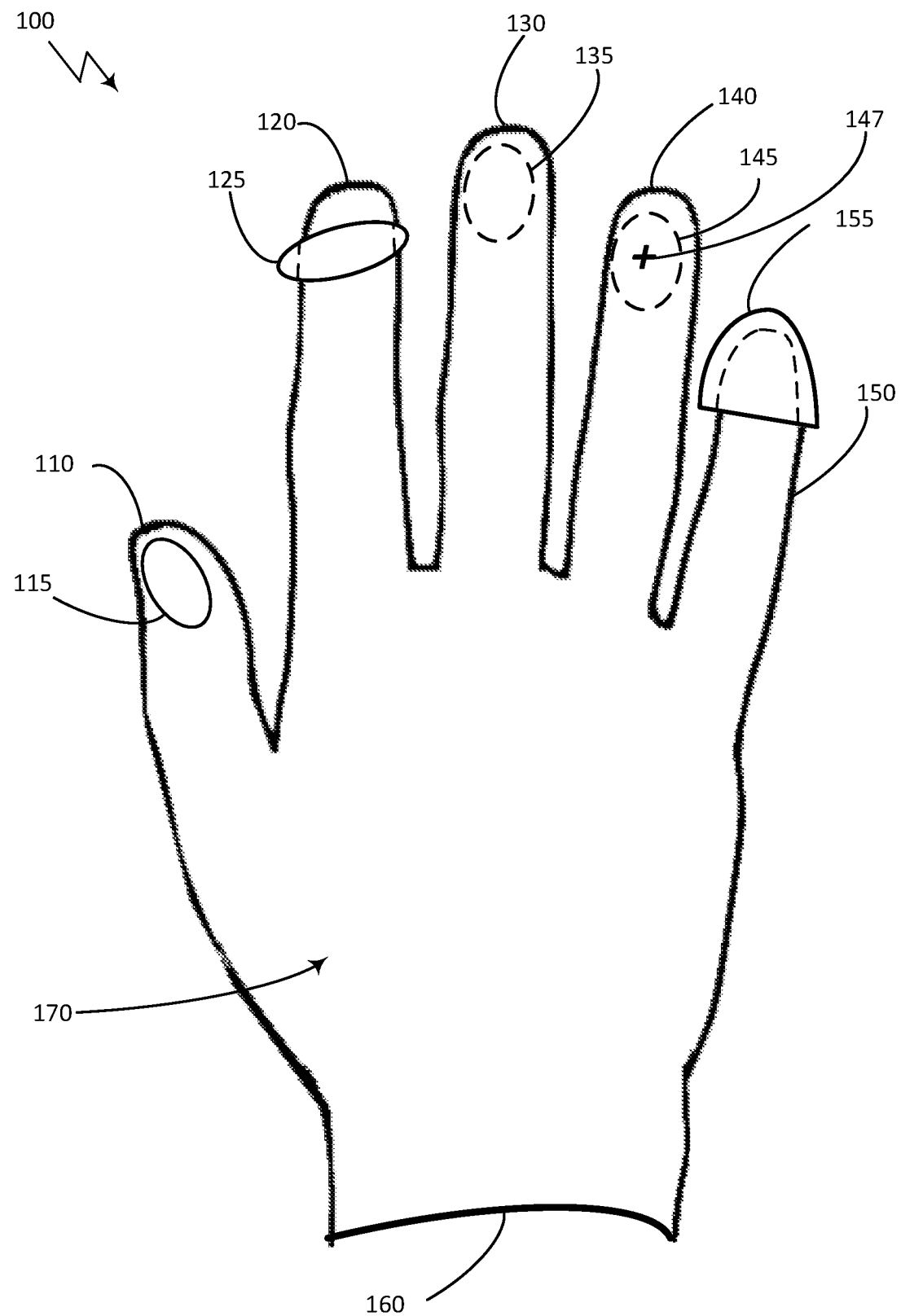

PADDED MEDICAL PROCEDURE GLOVE

CROSS REFERENCE TO RELATED APPLICATIONS

This application claims the benefit of priority to U.S. Provisional Patent Application Ser. No. 62/391,298, filed Apr. 25, 2016, titled "Medical exam glove and finger cot with added protection for fingernail bed and fingertip," the content of which is hereby incorporated by reference in its entirety.

FIELD OF THE DISCLOSURE

This application pertains to gloves and finger cots for use, e.g., in medical examination, surgery, and laboratory procedures.

SUMMARY

A glove may be formed of a polymer and include one or more pads over the back side of one or more distal finger joints. The glove or cot may optionally be lubricated, sterile, reversible and/or disposable, and may incorporate indicia indicating the location of the pads. The pads may provide protection from, e.g., repetitive stresses in tapping vials or syringes in medical examination, surgery, laboratory procedures, or other clinical contexts.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

A more detailed understanding may be had from the following description, given by way of example in conjunction with the accompanying figures. The figures are not necessarily drawn to scale.

FIG. 1 illustrates an example glove with a variety of pads.

FIG. 2 illustrates a number of finger cots with a variety of pads.

DETAILED DESCRIPTION OF ILLUSTRATIVE EMBODIMENTS

A glove may be formed of a polymer and include one or more pads over the back side of one or more distal finger joints. The glove may optionally be lubricated, sterile, reversible and/or disposable, and may incorporate indicia indicating the location of the pads. The pads may provide protection from, e.g., repetitive stresses in tapping vials or syringes in medical examination, surgery, laboratory procedures, or other clinical contexts.

Certain repetitive activities can create difficulties for practitioners in medical fields. For example, frequently tapping on vials, syringes, or laboratory glassware to liberate gas bubbles or trigger precipitation can cause stress, pain, or damage to the hand or fingers. Such issues may be partly or wholly alleviated with the use of gloves or finger cots with appropriately formed and positioned pads.

FIG. 1 shows an example glove 100 illustrating a number of ways in which padding may be applied to a finger cot or glove. The thumb 110 has a pad 115 which is visible from the exterior of the glove 100. In practice, a pad such as pad 115 may be may be affixed to the exterior body 170 of the glove, affixed to the interior of the glove, or formed as an integral part of the glove, for example. The index finger 120 has a pad 125 in the form of a band or ring surrounding the first joint of the index finger 120. In this example, the pad 125 is shown as being place around the glove 100. Alternatively, in practice the pad 125 may be formed within the glove 100 or affixed to the interior of the glove 100.

The middle finger 130 has a pad 135 which is not visible on the exterior of the glove 100. The pad 135 may be formed integrally with the glove 100 or affixed to the interior of the glove 100. The ring finger 140 similarly has a pad 145 which is not visible on the exterior of the glove. The ring finger 140 additionally has an indicia 147 by which a user of the glove may know where the pad 145 is located. In the example of FIG. 1, the indicia 147 is a small cross. In practice, an indicia may take the form of a print dot, line, or emblem, or a textured surface, for example, or any other suitable indicator. An indicia may be placed on any pad, whether the pad is visible on the exterior of a glove or not, and may additionally be placed on the interior surface of the glove to allow reversibility. The pinkie 150 has a pad 155 in the form of a cap over the end of the pinkie 150. The pad 155 provide protection both to the palm and back side of the glove 100. In this example, the pad 155 is shown as being placed over the body of the glove 100. In practice, the pad 155 may alternatively be formed integrally with the glove 100, e.g., molding it into the glove 100, or affixed to the interior of the glove 100.

In practice, a glove may incorporate any number of pads of any style at any location on the glove. It may be preferred to use a single style of pad. For example, optionally a pad integrally formed into the glove, and covered on both sides by the polymer material of the body of the glove, may provide the best options for sterilizing the glove. It may be preferred to place the pads only over the distal joints of a few fingers on the back of the hand. For example, pads may optionally be placed only over the nail and second joint of the middle and ring fingers, e.g., for use in tapping vials, syringes, or glassware, with no pads over the finger tips on the palm side of the hand. This would allow greater sensitivity and dexterity in manipulating objects.

FIG. 2 shows a set of example finger cots 200 illustrating a number of ways in which padding may be applied to cots. The cot 210 has a pad 215 which is visible from the exterior of the cot 210. In practice, a pad such as pad 215 may be may be affixed to the exterior of the cot, affixed to the interior of the cot, or formed as an integral part of the cot, for example. The cot 220 has a pad 225 in the form of a band or ring surrounding the first joint of the finger. In this example, the pad 225 is shown as being placed around the cot 220. Alternatively, in practice, the pad 225 may be formed within the cot 220 or affixed to the interior of the cot 220.

The cot 230 has a pad 235 which is not visible on the exterior of the cot 230. The pad 235 may be formed integrally with the cot 200 or affixed to the interior of the cot 230. The cot 240 similarly has a pad 245 which is not visible on the exterior of the cot 240. The cot 240 additionally has an indicia 247 by which a user of the cot 240 may know where the pad 245 is located. In the example of FIG. 2, the indicia 247 is a small cross. Again, in practice, an indicia may take the form of a print dot, line, or emblem, or a textured surface, for example, or any other suitable indicator. An indicia may be placed on any pad, whether the pad is visible on the exterior of a cot or not, and may additionally be placed on the interior surface of the cot to allow reversibility. The cot 250 has a pad 255 in the form of a cap over the end of the pinkie 250. The pad 255 provide protection both to the palm and back side of the cot 250. In this example, the pad 255 is shown as being place over the body of the cot 250. In practice, the pad 255 may alternatively be formed integrally with the cot, e.g., molding it into the cot 250, or affixed to the interior of the cot 250.

As with gloves, a finger cot may incorporate any number of pads of any style at any location on the cot.

The gloves and finger cots described herein may be of any thickness. For example, heavy duty medical examination gloves may have a general thickness of ten mils (i.e., 0.010 inches) or more, whereas surgical gloves may be as thin as two mils or thinner.

The pads of the gloves and finger cots described herein may be of any size and thickness. Generally, it is advantageous for the pads to generally cover the back of at least one joint of the finger the pad protects, e.g., where the finger would contact a vial or syringe when tapping on the vial or syringe. The pads may be thin, e.g., on the order of the thickness of the glove or cot generally. This may be acceptable when hard pad materials are used. Generally, thickness pads may be preferred, e.g., when made of impact absorbing rubbers or other polymers, like those materials used to form the glove or cot generally. In such cases, the pads may be many times thicker than the glove material, e.g., at least 25 mils thick, or 50, or 125 mils, i.e., ⅛ of an inch thick, or more.

The pads may be made of any material. Cotton or poly fill may be used, for example, as well as plastics, polymers, gels.

The gloves described herein may be of any length. For example, a short glove may measure seven inches from the tip of the middle finger to a cuff at the wrist. A standard glove may measure nine inches, for inches. A long glove may measure twelve inches, and a gauntlet may measure sixteen inches.

The gloves described herein may be reversible. For example, the padding may be integral to the glove such that the padding material is exposed neither to the interior or exterior surface of the glove. Alternatively, the padding may be of the same material as the glove. Thus, for purposes of protection or sterility, for example, it would not matter whether the glove or finger cot were worn right-side-out or inside-out. For example, indicia indicating the location of padding may be placed both on the interior and exterior of the glove to facilitate location of the pad when the glove or finger cot is worn right-side-out or inside-out.

The gloves and finger cots described herein may vary in thickness from one part to another. For example, an examination glove that is generally six mils thick, e.g., across the back of the hand, may have thicker areas, such as dots or ridges, at points on the palm or finger tips.

The gloves and finger cots described herein may be made of any suitable material. Safety gloves and cots, including gloves and cots used for medical and laboratory purposes may be made of natural and artificial latex, nitrile rubber, polyvinyl chloride, neoprene, isoprene, and polyisoprene, for instance. The pads for the gloves and cots may be may of similar materials or plastics, for instance.

The gloves and finger cots described herein may be lubricated or unlubricated. Cornstarch and lycopodium powder may be used as lubricants. For purposes of sterility, lubricants may be omitted.

In describing embodiments of the subject matter of the present disclosure, as illustrated in the figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A glove consisting of:
    a palm side and a back side, the palm side and the back side together providing a continuous outer covering made of a polymer selected from the list consisting of: latex, nitrile rubber; polyvinyl chloride; neoprene; isoprene; and polyisoprene, the glove configured to extend over a palm and back of a human hand and to extend to a wrist;
    a thumb sleeve, an index finger sleeve, a middle finger sleeve, a ring finger sleeve, and a pinkie finger sleeve;
    a first pad and a second pad, made of the polymer with a thickness of 20 mils or greater, the first pad integrated with the middle finger sleeve on the back side,
    the first pad located at a distal portion of the middle finger sleeve, the first pad configured to extend over a fingernail and a second joint of a middle finger of the human hand when worn;
    the second pad integrated with the ring finger sleeve on the back side;
    the second pad located at a distal portion of the ring finger sleeve, the second pad configured to extend over a fingernail and a second joint of a ring finger of the human hand when worn,
    a thickness of the continuous outer covering being in a range of 1 to 15 mils.

2. The glove of claim 1, where the glove is a medical examination glove.

3. The glove of claim 1, where the glove is a surgical glove.

4. The glove of claim 1, where the glove is sterile.

5. The glove of claim 1, where the glove is disposable.

* * * * *